United States Patent [19]

Heeres

[11] Patent Number: 4,539,325

[45] Date of Patent: Sep. 3, 1985

[54] 1-(2-ARYL-2-HALO-1-ETHENYL)-1H-AZOLES, AND ANTICONVULSANT USE THEREOF

[75] Inventor: Jan Heeres, Vosselaar, Belgium

[73] Assignee: Janssen Pharmaceutica N.V., Beerse, Belgium

[21] Appl. No.: 630,158

[22] Filed: Jul. 12, 1984

Related U.S. Application Data

[63] Continuation-in-part of Ser. No. 549,127, Nov. 7, 1983, abandoned.

[51] Int. Cl.$^3$ .................... A61J 31/41; A61J 31/415; C07D 233/61; C07D 233/54
[52] U.S. Cl. ................................ 514/283; 514/397; 514/399; 548/262; 548/336; 548/341
[58] Field of Search .......................... 424/269, 273 R; 548/262, 336, 341; 514/283, 397, 399

[56] References Cited

FOREIGN PATENT DOCUMENTS

| 8804 | 3/1980 | European Pat. Off. | ............ 548/336 |
| 60223 | 9/1982 | European Pat. Off. | ............ 548/336 |
| 61798 | 11/1983 | European Pat. Off. | ............ 548/336 |
| 1533705 | 11/1978 | United Kingdom | ................ 548/336 |

OTHER PUBLICATIONS

Kunz et al., C.A., vol. 98, 1983, 89361n, p. 560.
Gist–Brocades, C.A., vol. 97, 1982, 92276y, p. 771.
Jaeger et al., C.A., vol. 93, 1980, 210264k, p. 367.

*Primary Examiner*—Henry R. Jiles
*Assistant Examiner*—J. G. Mullins
*Attorney, Agent, or Firm*—Geoffrey G. Dellenbaugh

[57] ABSTRACT

1-(2-Aryl-2-halo-1-ethenyl)-1H-azoles having anticonvulsant properties which are particularly useful in the treatment of generalized forms of epilepsy.

12 Claims, No Drawings

1-(2-ARYL-2-HALO-1-ETHENYL)-1H-AZOLES, AND ANTICONVULSANT USE THEREOF

CROSS-REFERENCE TO RELATED APPLICATIONS

This is a continuation-in-part of our co-pending application Ser. No. 549,127, filed Nov. 7, 1983 now abandoned.

BACKGROUND OF THE INVENTION

A number of 1-(2-Ar-1-ethenyl)-1H-azoles have been described in
European Pat. No. 60-223;
European Pat. No. 61-798; and
European Pat. No. 8-804;
wherein said compounds are taught to be useful intermediates or antimicrobial agents.

The compounds of the present invention differ therefrom essentially by their unexpected anticonvulsant properties and by the nature of the substituents attached to the 2-Ar-1-ethenyl group since they invariably contain a halo-atom in the 2-position of said ethenyl group.

DESCRIPTION OF THE PREFERRED EMBODIMENTS

The present invention is concerned with 1-(2-Ar-2-halo-1-ethenyl)-1H-azoles having the formula $$\begin{array}{c} \text{(I)} \\ Q\diagdown_N\diagup^N \\ \underset{R}{\overset{|}{C}}=\underset{halo}{\overset{Ar}{C}} \end{array}$$

the pharmaceutically acceptable acid addition salts and the stereohemioally isomeric forms thereof, wherein
Q is CH or N;
R is hydrogen, lower alkyl, aryl, aryllower alkyl or halo; and
Ar is aryl;
wherein aryl is phenyl, substituted phenyl, naphthalenyl, substituted naphthalenyl, thienyl or substituted thienyl, wherein said substituted naphthalenyl and substituted thienyl are naphthalenyl, respectively thienyl, having 1 or 2 substituents each independently selected from the group consisting of halo, lower alkyl and lower alkyloxy and wherein said substituted phenyl is phenyl having from 1 to 3 substituents each independently selected from the group consisting of halo, lower alkyl, lower alkyloxy, trifluoromethyl, nitro, amino, phenyllower alkyl and a radical $R^2$, said $R^2$ being phenyl optionally substituted with halo and/or lower alkyl; provided that not more than one substituent on said substituted phenyl is a radical $R^2$.

As used in the foregoing definitions the term halo is generic to fluoro, chloro, bromo and iodo; and "lower alkyl" is meant to include straight and branched saturated hydrocarbon radicals, having from 1 to 6 carbon atoms, such as, for example, methyl, ethyl, 1-methylethyl, 1,1-dimethylethyl, propyl, butyl, pentyl, hexyl and the like.

Preferred compounds within the invention are those wherein Ar is phenyl being substituted with 1 or 2 halo atoms.

Particularly preferred compounds are those wherein Q is CH and Ar is phenyl substituted with 1 or 2 halo atoms.

The most preferred compounds are selected from the group consisting of 1-[2-chloro-2-(2,4-dichlorophenyl)ethenyl]-1H-imidazole, the pharmaceutically acceptable acid addition salts and the stereochemically isomeric forms thereof.

The compounds of formula (I) can generally be prepared by reacting an intermediate of formula (II) with a suitable halogenating agent.

$$\underset{(II)}{\begin{array}{c} Q\diagdown_N\diagup^N \\ \underset{R}{\overset{|}{-}}CH-\underset{\|}{\overset{O}{C}}-Ar \end{array}} \xrightarrow{\text{halogenating agent}} \underset{(I)}{\begin{array}{c} Q\diagdown_N\diagup^N \\ \underset{R}{\overset{|}{-}}C=\underset{halo}{\overset{}{C}}-Ar \end{array}}$$

Suitable halogenating agents are for example phosphorus halogenides, e.g. pentachlorophosphorane, pentabromophosphorane, phosphorous trichloride, phosphorous tribromide, phosphoryl chloride, phosphoryl bromide, dichlorotriphenylphosphorane, dibromotriphenylphosphorane, 2-chloro-1,3,2-benzodioxaphosphole, 2,2,2-trichloro-2,2-dihydro-1,3,2-benzodioxaphosphole and the like; molecular halogens, if desired in the presence of a suitable agent, such as for example hydrazine or a hydrazine derivative, e.g. phenylhydrazine and the like, a phosphine, e.g. triphenylphosphine and the like; sulfur halogenides, e.g. thionyl chloride, thionyl bromide, sulfuryl chloride, sulfuryl bromide and the like; carbonic dichloride, carbonic dichloride in the presence of a suitable agent such as, for example, a phosphine oxide, e.g. triphenylphosphine oxide and the like; metal halogenides such as, for example, titanium tetrachloride, zinc chloride and the like; a tetrahalomethane in the presence of phosphine, e.g. tetrachloromethane and the like in the presence of triphenylphosphine and the like; and mixtures of said halogenating agents. The halogenating reaction may be conducted in a suitable solvent such as for example, an aliphatic hydrocarbon, e.g. hexane, heptane, octane, cyclohexane and the like; an aromatic hydrocarbon, e.g. benzene, methylbenzene, dimethylbenzene and the like; an ether, e.g. 1,4-dioxane, tetrahydrofuran, 1,1'-oxybisethane and the like; an halogenated hydrocarbon, e.g. dichloromethane, trichloromethane, 1,2-dichloroethane, 1,1,2,2-tetrachloroethane; and mixtures of such solvents. Somewhat elevated temperatures may enhance the rate of the reaction.

Depending on the reaction circumstances there may be prepared compounds of formula (I) wherein R is halo, said compounds being represented by the formula (I-a), by reacting an intermediate of formula (II), wherein R is hydrogen, said intermediates being represented by the formula (II-a) with an appropriate halogenating agent in the presence of a suitable solvent as described hereinabove for the preparation of (I) starting from (II).

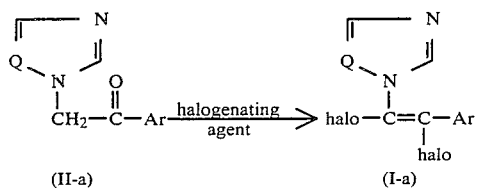

The compounds of formula (I) can also be converted into each other following art-known procedures of functional grouptransformation.

In all of the foregoing and in the following preparations, the reaction products may be isolated from the reaction mixture and, if necessary, further purified according to methodologies generally known in the art.

From formula (I) it is evident that the compounds of this invention may be present as E- or Z-forms, this E and Z notation being in correspondence with the rules described in "International Union of Pure and Applied Chemistry: Tentative Rules for the Nomenclature of Organic Chemistry. Section E. Fundamental Stereochemistry" in J. Org. Chem., 35, 2849–2867 (1970).

Pure stereochemically isomeric forms of the compounds of formula (I) may be obtained by the application of art-known separation methods such as selective crystallization and chromatographic techniques, e.g., counter current distribution, column chromatography, high performance liquid chromatography and the like.

In some compounds the stereochemical configuration is not experimentally determined. In those cases it is conventionally agreed to designate the stereochemically isomeric form which is first isolated as "A" and the second as "B", without further reference to the actual stereochemical configuration.

Stereochemically isomeric forms of the compounds of formula (I) are naturally intended to be embraced within the scope of the invention.

The compounds of formula (I) have basic properties and, consequently, they may be converted to their therapeutically active nontoxic acid addition salt forms by treatment with appropriate acids, such as, for example, inorganic acids, such as hydrohalic acid, e.g. hydrochloric, hydrobromic and the like, sulfuric acid, nitric acid, phosphoric acid and the like; or organic acids, such as, for example, acetic, propanoic, hydroxyacetic, 2-hydroxy-propanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The intermediates of formula (II) can be prepared following the procedures described in British Pat. No. 1,553,705.

The useful anticonvulsant properties of the compounds of formula (I), the acid addition salts and the stereochemically isomeric forms thereof are illustrated in the Maximal Metrazol Seizure test.

Metrazol (pentylenetetrazol) has been described as a convulsion inducing agent in, for example, Drug Res. 26, No. 8, 1592–1603 (1976). The protection from the various types of seizures induced by metrazol appears to be a good method for evaluating quantitatively the anticonvulsant potential of the test compounds.

DESCRIPTION OF THE MAXIMAL METRAZOL TEST

Female Wistar rats weighing 115±5 g were starved overnight having water ad libitum. To each rat an aqueous mixture containing the test compound was administered via the intraperitoneal route. One hour after drug-treatment Maximal Metrazol Seizures were induced by a rapid injection of 80 mg/kg body weight pentylenetetrazol at a volume of 0.4 ml/100 g body weight in a tail vein. The lowest effective dose of the test compounds capable of antagonizing CLO (generalized clonic seizures), TFP (tonic backwards extension of the forepaws) and THP (tonic hindpaw extension) are listed in Table 1, in the first, respectively second and third column.

The compounds listed in Table 1 are not given for the purpose of limiting the invention thereto but only to exemplify the useful pharmacological activities of all the compounds within the scope of formula (I).

TABLE 1

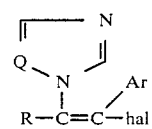

| No. | Q | R | hal | Ar | Isomeric form | Column 1 | Column 2 | Column 3 |
|---|---|---|---|---|---|---|---|---|
| 1* | CH | H | Cl | 2,4-$Cl_2$—$C_6H_3$ | Z | 2.5 | 2.5 | 2.5 |
| 67* | CH | H | Br | 2,4-$Cl_2$—$C_6H_3$ | E + Z | 10 | 10 | 10 |
| 13* | CH | H | Cl | 2-Cl,4-F—$C_6H_3$ | — | — | — | 10 |
| 68** | CH | H | Br | 2,4-$Cl_2$—$C_6H_3$ | Z | — | — | 0.63 |
| 14* | CH | H | Cl | 4-F—$C_6H_4$ | — | — | — | 2.5 |
| 38* | CH | H | Cl | 2,4-$Br_2$—$C_6H_3$ | Z | 5 | 5 | 1.25 |
| 19* | CH | H | Cl | 4-Br,2-Cl—$C_6H_3$ | Z | 10 | 10 | 5 |
| 65* | CH | H | Cl | 2-naphthalenyl | Z | — | — | 2.5 |
| 63* | N | Cl | Cl | 2,4-$Br_2$—$C_6H_3$ | E | 10 | 10 | 10 |
| 47* | CH | H | Cl | 2-Br,4-$CH_3O$—$C_6H_3$ | Z | — | — | 5 |
| 24*** | CH | H | Cl | 2,4-$Cl_2$—$C_6H_3$ | E | — | — | 2.5 |

TABLE 1-continued $$\begin{array}{c} Q\diagdown\underset{\underset{R-C=C-hal}{|}}{N}\diagup\underset{Ar}{\overset{N}{\diagdown}}\end{array}$$

| | | | | | Iso- | lowest effective dose in mg/kg body weight to antagonize: CLO, TFP, THP | | |
|---|---|---|---|---|---|---|---|---|
| No. | Q | R | hal | Ar | meric form | Column 1 | Column 2 | Column 3 |
| 61* | CH | H | Cl | 3-CF$_3$—C$_6$H$_4$ | Z | — | — | ≦10 |

*HNO$_3$—salt
**(COOH)$_2$—salt
***HCl—salt

In view of their anticonvulsant properties, the compounds of formula (I), their acid addition salts and stereochemically isomeric forms thereof are very useful in the treatment of convulsions, and more particularly, in the treatment of generalized forms of epilepsy. In addition to the hereinabove-mentioned anticonvulsant activity, the compounds of formula (I) are particularly interesting agents due to their useful antihypoxic activity.

In view of their useful anticonvulsant activity, the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following formulations exemplify typical pharmaceutical compositions in dosage unit form suitable for systemic administration to animal and human subjects in accordance with the present invention. These formulations are given to illustrate and not to limit the scope of the present invention.

"Active ingredient" (A.I.) as used throughout these formulations relates to a compound of formula (I), a possible stereochemically isomeric form or pharmaceutically acceptable acid addition salt thereof.

ORAL DROPS

500 Grams of the A.I. was dissolved in 0.5 liters of 2-hydroxypropanoic acid and 1.5 liters of the polyethylene glycol at 60°–80° C. After cooling to 30°–40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

ORAL SOLUTION

9 Grams of methyl 4-hydroxybenzoate and 1 gram of propyl 4-hydroxybenzoate were dissolved in 4 liters of boiling purified water. In 3 liters of this solution were dissolved first 10 grams of 2,3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of the active ingredient per teaspoonful (5 milliliters). The resulting solution was filled in suitable containers.

CAPSULES

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

FILM-COATED TABLETS

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 milliliters of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 milligrams of the active ingredient.

Coating

To a solution of 10 grams methyl cellulose in 75 milliliters of denaturated ethanol there was added a solution of 5 grams of ethyl cellulose in 150 milliliters of dichloromethane. Then there were added 75 milliliters of dichloromethane and 2.5 milliliters 1,2,3-propanetriol. 10 Grams of polyethylene glycol was molten and dissolved in 75 milliliters of dichloromethane. The latter solution was added to the former and then there were added 2.5 grams of magnesium octadecanoate, 5 grams of polyvinylpyrrolidone and 30 milliliters of concentrated colour suspension (Opaspray K-1-2109) and the whole was homogenated. The tablet cores were coated with the thus obtained mixture in a coating apparatus.

INJECTABLE SOLUTION 1.8 Grams methyl 4-hydroxybenzoate and 0.2 grams propyl 4-hydroxybenzoate were dissolved in about 0.5 liters of boiling water for injection. After cooling to about 50° C. there were added while stirring 4 grams lactic acid, 0.05 propylene glycol and 4 grams of the A.I. The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

SUPPOSITORIES

3 Grams A.I. was dissolved in a solution of 3 grams 2,3-dihydroxybutanedioic acid in 25 milliliters polyethylene glycol 400. 12 Grams surfactant and triglycerides q.s. ad 300 grams were molten together. The latter mixture was mixed well with the former solution. The thus obtained mixture was poured onto moulds at a temperature of 37°-38° C. to form 100 suppositories each containing 30 milligrams of the active ingredient.

The present invention is also related with a method of treating convulsions in warm-blooded animals suffering from said convulsions by administering an effective anticonvulsant amount of a compound of formula (I) or a pharmaceutically acceptable acid addition salt thereof.

Suitable doses administered daily to subjects are varying from 0.1 to 500 mg, more preferably from 1 to 100 mg.

The following examples are intended to illustrate and not to limit the scope of the present invention. Unless otherwise stated all parts therein are by weight.

EXAMPLES

A. Intermediates

The preparation of the intermediates of formula (II) is described in British Pat. No. 1,553,705.

B. Final Products

Example 1

A mixture of 10 parts of 1-(2,4-dichlorophenyl)-2-(1H-imidazol-1-yl)ethanone monohydrochloride and 10 parts of pentachlorophosphorane was stirred and refluxed for 1 hour. The reaction mixture was allowed to cool and treated with ice water. The whole was neutralized with potassium carbonate and the product was extracted twice with 2,2'-oxybispropane. The combined extracts were dried, filtered and evaporated. The residue was converted into the nitrate salt in 4-methyl-2-pentanone. The salt was filtered off and crystallized from ethanol, yielding 5.1 parts (40%) of (Z)-1-[2-chloro-2-(2,4-dichlorophenyl)ethenyl]-1H-imidazole mononitrate; mp. 161.4° C. (compound 1).

Example 2

To a stirred mixture of 20.2 parts of (Z)-1-[2-chloro-2-(2,4-dichlorophenyl)ethenyl]-1H-imidazole mononitrate, 100 parts of water and 70 parts of 2,2'-oxybispropane were added 5 parts of ammonium hydroxide. The whole was stirred for 15 minutes. The layers were separated. The aqueous phase was extracted with 35 parts of 2,2'-oxybispropane. The combined organic layers were washed with water, dried, filtered and evaporated, yielding 15.9 parts of (Z)-1-[2-chloro-2-(2,4-dichlorophenyl)ethenyl]-1H-imidazole; mp. 59.1° C. (compound 2).

Example 3

To a stirred mixture of 12.76 parts of (Z)-1-[2-chloro-2-(2,4-dichlorophenyl)ethenyl]-1H-imidazole mononitrate, 120 parts of water and 70 parts of 2,2'-oxybispropane were added 3.5 parts of ammonium hydroxide. The whole was stirred till homogeneous. The layers were separated. The aqueous phase was extracted with 35 parts of 2,2'-oxybispropane. The combined organic layers were washed with water, dried, filtered and evaporated in vacuo. The residue was converted into the hydrochloride salt in 64 parts of 2-propanone. The salt was filtered off, washed with 2-propanone and dried in vacuo, yielding 8.54 parts of (Z)-1-[2-chloro-2-(2,4-dichlorophenyl)ethenyl]-1H-imidazole monohydrochloride; mp. 178.8° C. (compound 3).

Example 4

A mixture of 10 parts of 1-(2,6-dichlorophenyl)-2-(1H-imidazol-1-yl)ethanone monohydrochloride and 20 parts of pentachlorophosphorane was stirred and refluxed for 3 hour. The solution was diluted with dichloromethane and 300 parts of water were added dropwise during a 1 hour period. The whole was neutralized with potassium carbonate. The product was extracted twice with dichloromethane. The extract was dried, filtered and evaporated. The residue was purified by column chromatography over silica gel using dichloromethane as eluent. The pure fractions were collected and the eluent was evaporated. The residue was converted into the nitrate salt in 4-methyl-2-pentanone and 2,2'-oxybispropane. The salt was filtered off and crystallized from 4-methyl-2-pentanone, yielding 4.6 parts (40%) of (E+Z)-1-[2-chloro-2-(2,6-dichlorophenyl)ethenyl]-1H-imidazole mononitrate; mp. 122.3° C. (compound 4).

In a similar manner there were also prepared:

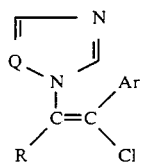

| Comp. No. | Q | R | Ar | Isomeric form | Base or Salt | mp. °C. |
|---|---|---|---|---|---|---|
| 5 | CH | H | 2-Cl—C$_6$H$_4$ | E + Z | HNO$_3$ | 111.4 |
| 6 | CH | CH$_3$ | 2,4-Cl$_2$—C$_6$H$_3$ | E + Z | HNO$_3$ | 112.0 |
| 7 | CH | 2,4-Cl$_2$—C$_6$H$_3$CH$_2$ | 4-Cl—C$_6$H$_4$ | — | HNO$_3$ | 161.3 |
| 8 | N | H | 2,4-Cl$_2$—C$_6$H$_3$ | — | HNO$_3$ | 145.7 |
| 9 | CH | H | 4-F—C$_6$H$_4$ | — | base | 102.2 |
| 10 | CH | H | 4-Cl—C$_6$H$_4$ | — | base | 102.6 |
| 11 | CH | CH$_3$ | 4-Br—C$_6$H$_4$ | E | (COOH)$_2$ | 125.6 |
| 12 | CH | H | 5-Cl—2-thienyl | B | HNO$_3$ | 148.6 |
| 13 | CH | H | 2-Cl,4-F—C$_6$H$_3$ | — | HNO$_3$ | 140.1 |
| 14 | CH | H | 4-F—C$_6$H$_4$ | — | HNO$_3$ | 156.4 |
| 15 | CH | H | 2-Cl,4-CH$_3$OC$_6$H$_3$ | A + B | HNO$_3$ | 135.3 |
| 16 | CH | H | 2,3,4-Cl$_3$—C$_6$H$_2$ | — | HNO$_3$ | 170.2 |
| 17 | CH | H | 4-Br—C$_6$H$_4$ | — | HNO$_3$ | 163.5 |
| 18 | CH | H | 2,4-Cl$_2$—C$_6$H$_3$ | E | HNO$_3$ | 145.1 |
| 19 | CH | H | 4-Br,2-Cl—C$_6$H$_3$ | Z | HNO$_3$ | 166.1 |
| 20 | CH | H | 3,4-Cl$_2$—C$_6$H$_3$ | Z | HNO$_3$ | 168.7 |
| 21 | CH | H | 4-Br,2-Cl—C$_6$H$_3$ | E | HNO$_3$ | 150.0 |
| 22 and | CH | H | 2,4,5-Cl$_3$—C$_6$H$_2$ | Z | HNO$_3$ | 156.9 |
| 23 | CH | H | 3,4-Cl$_2$—C$_6$H$_3$ | E | HNO$_3$ | 145.6 |

Example 5

To a stirred mixture of 1.9 parts of (E)-1-[2-chloro-2-(2,4-dichlorophenyl)ethenyl]-1H-imidazole mononitrate in a mixture of 50 parts of water and 75 parts of trichloromethane was added 1.0 part of potassium carbonate. The whole was stirred till a clear solution was obtained (pH 8-9). The organic layer was separated, dried, filtered and evaporated. The residue was converted into the hydrochloride salt in 4-methyl-2-pentanone, 2,2'-oxybispropane and 2-propanol. The salt was filtered off and dried, yielding 1.5 parts (86%) of (E)-1-[2-chloro-2-(2,4-dichlorophenyl)ethenyl]-1H-imidazole monohydrochloride; mp. 203.2° C. (compound 24).

Example 6

A mixture of 30 parts of 1-(2-methoxyphenyl)-2-(1H-imidazol-1-yl)ethanone hydrochloride and 60 parts of pentachlorophosphorane was stirred and refluxed for 3 hours. The reaction mixture was diluted with 600 parts of dichloromethane and 100 parts of potassium carbonate were added. Then water was added dropwise during a 2 hours period. The product was extracted three times with dichloromethane. The combined extracts were dried, filtered and evaporated. The residue was purified by column chromatography over silica gel using trichloromethane as eluent. The pure fractions were collected and the eluent was evaporated. The residue was crystallized from 2,2'-oxybispropane, yielding 7 parts (22%) of 1-[1,2-dichloro-2-(2-methoxyphenyl)ethenyl]-1H-imidazole; mp. 101.4° C. (compound 25).

In a similar manner there were also prepared:

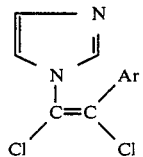

| Comp. No. | Ar | Isomeric form | Base or Salt | mp. °C. |
|---|---|---|---|---|
| 26 | 4-CH$_3$—C$_6$H$_4$ | — | HNO$_3$ | 153.0 |
| 27 | 2-Cl—C$_6$H$_4$ | — | 1½ (COOH)$_2$ | 139.0 |
| 28 | C$_6$H$_5$ | E + Z | HNO$_3$ | 130.5 |
| 29 | 4-F—C$_6$H$_4$ | — | HNO$_3$ | 131.4 |
| 30 | 5-chloro-2-thienyl | A | HNO$_3$ | 143.1 |
| 31 | 5-chloro-2-thienyl | B | HNO$_3$ | 142.3 |
| 32 | 4-Br—C$_6$H$_4$ | A | — | 131.1 |
| 33 | 2,4-Br$_2$—C$_6$H$_3$ | — | HNO$_3$ | 136.2 |
| 34 | 3,4-Cl$_2$—C$_6$H$_3$ | — | (COOH)$_2$ | 143.8° C. and |
| 35 | 3,4-Cl$_2$—C$_6$H$_3$ | — | HNO$_3$ | 148.3 |

Example 7

A mixture of 23.0 parts of 1-(2-bromo-4-chlorophenyl)-2-(1H-imidazol-1-yl)ethanone, 23.0 parts of pentachlorophosphorane and 17 parts of phosphoryl chloride was stirred and refluxed for 4 hours. The reaction mixture was cooled and diluted with 260 parts of dichloromethane. This solution was added dropwise, during a 2 hours period, to a solution of 300 parts of potassium carbonate in 500 parts of water. The whole was stirred overnight at room temperature. The product was extracted twice with 2,2'-oxybispropane. The combined extracts were dried, filtered and evaporated. The residue was converted into the nitrate salt in ethyl acetate and 2,2'-oxybispropane. The salt was filtered off and purified by reversed phase chromatography over LiChroprep. RP 18 using a mixture of methanol (containing 0.1% of N-(1-methylethyl)-2-propanamine) and water (containing 0.5% of ammonium acetate) (65:35 by volume) as eluent. The first fraction was collected and the eluent was evaporated. The residue was converted into the nitrate salt in a mixture of ethyl acetate and 2,2'-oxybispropane. The salt was filtered off and crystallized from 4-methyl-2-pentanone, yielding 2.9 parts (10%) of (E)-1-[2-(2-bromo-4-chlorophenyl)-2-chloroethenyl]-1H-imidazole mononitrate; mp. 162.9° C. (compound 36). The second fraction was collected and the eluent was evaporated. The residue was converted into the nitrate salt in a mixture of ethyl acetate and 2,2'-oxybispropane. The salt was filtered off and crystallized from 4-methyl-2-pentanone, yielding 3.3 parts (11%) of (Z)-1-[2-(2-bromo-4-chlorophenyl)-2-chloroethenyl]-1H-imidazole mononitrate; mp. 167.8° C. (compound 37).

In a similar manner there were also prepared:

(Z)-1-[2-chloro-2-(2,4-dibromophenyl)ethenyl]-1H-imidazole mononitrate; mp. 162.4° C. (compound 38); and (E)-1-[2-chloro-2-(2,4-dibromophenyl)ethenyl]-1H-imidazole mononitrate; mp. 170.4° C. (compound 39);

(Z)-1-[2-([1,1'-biphenyl]-4-yl)-2-chloroethenyl]-1H-imidazole mononitrate; mp. 186.5°-187.2° C. (compound 40); and (E)-1-[2-([1,1'-biphenyl]-4-yl)-2-chloroethenyl]-1H-imidazole mononitrate; mp. 155.7°-156.0° C. (compound 41);

(Z)-1-[2-chloro-2-(2-chloro-4methylphenyl)ethenyl]-1H-imidazole mononitrate; mp. 153.6° C. (compound 42); and (E)-1-[2-chloro-2-(2-chloro-4-methylphenyl)ethenyl]-1H-imidazole mononitrate; mp. 144.4° C. (compound 43).

Example 8

A mixture of 20 parts of 1-(4-bromo-2-chlorophenyl)-2-(1H-1,2,4-triazol-1-yl)ethanone, 40 parts of pentachlorophosphorane and 300 parts of 1,2-dichloroethane was stirred and relfuxed overnight. 300 Parts of potassium carbonate and 650 parts of dichloromethane were added and water was added dropwise carefully till a volume of about 1500 parts. The aqueous phase was extracted with dichloromethane. The combined organic layers were washed with water, dried, filtered and evaporated. The residue was purified by reversed phase chromatography (HPLC) over LiChroprep RP 18 using a mixture of 75% of methanol containing 0.1% of N-(1-methylethyl)-2-propanamine and 25% of water containing 0.5% of ammonium acetate. The first fraction (E-isomer) was collected and the eluent was evaporated. The residue was crystallized from hexane at 0° C. The product was filtered off and dried in vacuo at 60° C., yielding 7.9 parts (37%) of (E)-1-[2-(4-bromo-2-chlorophenyl)-2-chloroethenyl]-1H-1,2,4-triazole; mp. 84.0° C. (compound 44). The second fraction (Z-isomer) was collected and the eluent was evaporated. The residue was crystallized from hexane at 0° C. The product was filtered off and dried in vacuo at 60° C., yielding 0.36 parts of (Z)-1-[2-(4-bromo-2-chlorophenyl)-2-chloroethenyl]-1H-1,2,4-triazole; mp. 96.0° C. (compound 45).

Following the same procedure and using equivalent amounts of the appropriate starting materials, there were also prepared:

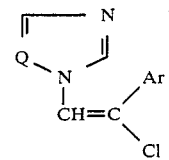

| Comp. No. | Q | Ar | Isomeric form | Base or Salt | mp. °C. |
|---|---|---|---|---|---|
| 46 | CH | 2-Br—4-CH₃O—C₆H₃ | E | HNO₃ | 133.8 |
| 47 | CH | 2-Br—4-CH₃O—C₆H₃ | Z | HNO₃ | 149.0 |
| 48 | CH | 4-(2-phenylethyl)phenyl | Z | HNO₃ | 183.5 |
| 49 | CH | 4-(2-phenylethyl)phenyl | E | HNO₃ | 128.5 |
| 50 | CH | 4-(phenylmethyl)phenyl | Z | HNO₃ | 140.7 |
| 51 | CH | 4-(phenylmethyl)phenyl | E | HNO₃ | 149.1 |
| 52 | CH | 2-F,4-CH₃O—C₆H₃ | E | HNO₃ | 135.9 |
| 53 | CH | 2-F,4-CH₃O—C₆H₃ | Z | HNO₃ | 140.5 |

In a similar manner there were also prepared:

(Z)-1-[2-chloro-1-(2,4-dichlorophenyl)-2-(4-fluorophenyl)ethenyl]-1H-imidazole; mp. 104.4° C. (54); and (E)-1-[2-chloro-1-(2,4-dichlorophenyl)-2-(4-fluorophenyl)ethenyl]-1H-imidazole; mp. 146.2° (55).

Example 9

A mixture of 18.7 parts of 2-(1H-imidazol-1-yl)-1-phenylethanone, 37.4 parts of phosphor pentachloride and 240 parts of 1,2-dichloroethane was stirred and refluxed for 4 hours. The mixture was diluted with dichloromethane. This solution was added dropwise, during a 2 hours period, to a solution of 350 parts of potassium carbonate in 500 parts of water. Upon completion, stirring was continued overnight. The organic layer was separated and the aqueous phase was extracted with dichloromethane. The combined organic layers were washed with water, dried, filtered and evaporated. The residue was converted into the nitrate salt in 4-methyl-2-pentanone. The salt was filtered off, triturated in 2-propanone, filtered off and crystallized from 2-propanol. The product was filtered off, the base was liberated with a potassium carbonate solution and extracted with trichloromethane. The extract was dried, filtered and evaporated. The residue was purified by column chromatography over silica gel using a mixture of methylbenzene and ethanol (98.5:1.5 by volume) as eluent. The pure fractions were collected and the eluent was evaporated. The residue was converted into the nitrate salt in 2,2'-oxybispropane. After stirring overnight, the salt was filtered off and crystallized from ethanol. The whole was allowed to stand overnight. The product was filtered off and dried in vacuo at 60° C., yielding 4 parts (14%) of (Z)-1-(2-chloro-2-phenylethenyl)-1H-imidazole mononitrate; mp. 144.0° C. (56).

In a similar manner there were also prepared:

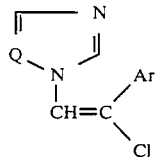

| Comp. No. | Q | Ar | Isomeric form | Base or Salt | mp. °C. |
|---|---|---|---|---|---|
| 57 | CH | 2-Cl—4-NO$_2$—C$_6$H$_3$ | E + Z | HNO$_3$ | 145.0 |
| 58 | N | 4-Cl—2-F—C$_6$H$_3$ | E | HNO$_3$ | 124.2 |
| 59 | N | 2,4-Br$_2$—C$_6$H$_3$ | E | base | 92.1 |
| 60 | N | 2,4-Br$_2$—C$_6$H$_3$ | E | HNO$_3$ | 114.1 |
| 61 | CH | 3-CF$_3$—C$_6$H$_4$ | Z | HNO$_3$ | 125.9 |

Example 10

A mixture of 35 parts of 1-(2,4-dibromophenyl)-2-(1H-1,2,4-triazol-1-yl)ethanone, 70 parts of pentachlorophosphorane and 180 parts of 1,2-dichloroethane was stirred and refluxed for 4 hours. After cooling, dichloromethane was added. The reaction mixture was added dropwise, during a 2 hours period, to a solution of 350 parts of potassium carbonate in 500 parts of water, while stirring. Upon completion, stirring was continued overnight. The product was extracted with dichloromethane. The extract was dried, filtered and evaporated to dry. The residue was converted into the nitrate salt in 2,2'-oxybispropane. The salt was filtered off (and set aside) and the filtrate was concentrated. To the concentrate, was added a small amount of nitric acid. The precipitated product was filtered off (the filtrate was set aside) and purified, together with the salt, which was set aside (see above), by reversed phase chromatography (HPLC) over LiChroprep RP 18 using a mixture of 70% of methanol containing 0.1% of N-(1-methylethyl)-2-propanamine and 30% of water containing 0.5% of ammonium acetate. The pure fractions were collected and the eluent was evaporated. The residue was crystallized from 2,2'-oxybispropane. The product was filtered off and the filtrate, together with the filtrate which was set aside, was neutralized with potassium carbonate. The product was extracted with trichloromethane. The extract was dried, filtered and evaporated. The oily residue was purified by column chromatography over silica gel using a mixture of methylbenzene and ethanol (99:1 by volume) as eluent. The first fraction (Z-isomer) was collected and the eluent was evaporated. The residue was treated with activated charcoal. The latter was filtered off and the filtrate was evaporated. The residue was converted into the nitrate salt in a small amount of 2,2'-oxybispropane and hexane. The precipitated product was stirred overnight. It was filtered off and dried in a dry-pistol at room temperature, yielding 4.4 parts (9%) of (Z)-1-[1,2-dichloro-2-(2,4-dibromophenyl)ethenyl]-1H-1,2,4-triazole mononitrate; mp. 98.1° C. (compound 62). The second fraction (E-isomer) was collected and the eluent was evaporated. The residue was treated with activated charcoal. The latter was filtered off and the filtrate was evaporated. The residue was converted into the nitrate salt in a small amount of 2,2'-oxybispropane and hexane. The precipitated product was stirred overnight. It was filtered off (the filtrate was set aside) and dried in a dry-pistol at room temperature, yielding a first fraction of 3.7 parts (7%) of (E)-1-[1,2-dichloro-2-(2,4-dibromophenyl)ethenyl]-1H-1,2,4-triazole mononitrate; mp. 126.3° C. (compound 63).

Example 11

A mixture of 29.0 parts of 1-(2-bromo-4-methoxyphenyl)-2-(1H-imidazol-1-yl)ethanone monohydrochloride, 58.0 parts of phosphor pentachloride and 360 parts of 1,2-dichloroethane was stirred and refluxed for 4 hours. The reaction mixture was cooled and diluted with dichloromethane. The resulting solution was added dropwise, during a 2 hours period, to a stirred solution of 300 parts of potassium carbonate in 500 parts of water. Upon completion, stirring was continued overnight at room temperature. The product was extracted twice with dichloromethane. The combined extracts were washed with water, dried, filtered and evaporated. The oily residue was purified by column chromatography over silica gel using a mixture of methylbenzene and trichloromethane (75:25 by volume) as eluent. The first fraction was collected and the eluent was evaporated. The residue was converted into the nitrate salt in ethyl acetate and 2,2'-oxybispropane. The salt was filtered off and crystallized from ethyl acetate, yielding, after drying overnight in vacuo at 80° C., 0.7 parts (1%) of 1-[2-(2-bromo-4-methoxyphenyl)-1,2-dichloroethenyl]-1H-imidazole mononitrate; mp. 124.9° C. (compound 64).

Example 12

A mixture of 30.0 parts of 2-(1H-imidazol-1-yl)-1-(2-naphthalenyl)ethanone, 60.0 parts of pentachlorophosphorane and 40 parts of 1,1,2,2-tetrachloroethane was stirred and refluxed for 4 hours. After cooling, the reaction mixture was diluted with 260 parts of dichloromethane and 300 parts of potassium carbonate were added. Then 250 parts of water were added dropwise, during a 2 hours period and subsequently more water was added. Upon completion, stirring was continued overnight at room temperature. The product was extracted twice with dichloromethane. The combined extracts were washed with water, dried, filtered and evaporated in vacuo. The residue as converted into the nitrate salt in 2-propanone and 2,2'-oxybispropane. The salt was filtered off and crystallized from ethanol (activated charcoal), yielding 7.9 parts (20%) of (Z)-1-[2-chloro-2-(2-naphthalenyl)ethenyl]-1H-imidazole mononitrate; mp. 150.1° C. (compound 65).

Example 13

A mixture of 30.0 parts of 2-(1H-imidazol-1-yl)-1-(2-naphthalenyl)ethanone, 60.0 parts of phosphor pentachloride and 40 parts of 1,1,2,2-tetrachloroethane was stirred and refluxed for 4 hours. After cooling, the reaction mixture was diluted with dichloromethane. Potassium carbonate was added and water was added dropwise, during a 2 hours period. Upon completion, another 500 parts of water were added and stirring was continued overnight. The product was extracted with methylbenzene. The organic layer was dried, filtered and evaporated in vacuo. The residue was purified by column chromatography over silica gel using a mixture of methylbenzene and trichloromethane (75:25 by volume) as eluent. The pure fractions were collected and the eluent was evaporated. The residue was converted into the nitrate salt in 4-methyl-2-pentanone and 2,2'-oxybispropane. The salt was filtered off and triturated in 2-propanone. The product was filtered off and crystallized from 2-propanone, yielding 1.3 parts of (E)-1-[2-chloro-2-(2-naphthalenyl)ethenyl]-1H-imidazole mononitrate; mp. 131.0° C. (compound 66).

Example 14

A mixture of 10.0 parts of 1-(2,4-dichlorophenyl)-2-(1H-imidazol-1-yl)ethanone monohydrochloride and 20.0 parts of pentabromophosphorane was stirred and refluxed for 3 hours. After cooling, the reaction mixture, was diluted with dichloromethane. 30.0 Parts of potassium carbonate were added followed by the dropwise addition of water during 2 hours. More water was added and the whole was neutralized with potassium carbonate. The product was extracted twice with dichloromethane. The combined extracts were dried, filtered and evaporated. The residue was purified by column chromatography over silica gel using dichloromethane as eluent. The pure fractions were collected and the eluent was evaporated. The residue was converted into the nitrate salt in 4-methyl-2-pentanone and 2,2'-oxybispropane. The salt was filtered off and crystallized from 4-methyl-2-pentanone, yielding 3.5 parts (27%) of (E+Z)-1-[2-bromo-2-(2,4-dichlorophenyl)ethenyl]-1H-imidazole mononitrate; mp. 137.9° C. (compound 67).

Example 15

A mixture of 15.6 parts of 1-(2,4-dichlorophenyl)-2-(1H-imidazol-1-yl)ethanone hydrochloride and 31.2 parts of phosphor pentabromide was stirred and refluxed for 4 hours. The reaction mixture was cooled and diluted with dichloromethane. This solution was added to a solution of 100 parts of potassium carbonate in water during a 2 hours period. Upon completion, stirring was continued overnight at room temperature. The product was extracted with dichloromethane. The extract was dried, filtered and evaporated. The residue was purified by column chromatography over silica gel using a mixture of dichloromethane and methylbenzene (50:50 by volume) as eluent. The first fraction was collected and the eluent was evaporated. The residue was converted into the ethanedioate salt in 4-methyl-2-pentanone and 2,2'-oxybispropane. The salt was filtered off and crystallized from 4-methyl-2-pentanone, yielding 1.9 parts (8%) of (Z)-1-[2-bromo-2-(2,4-dichlorophenyl)ethenyl]-1H-imidazoleethanedioate (1:1); mp. 183.4° C. (compound 68).

Example 16

A mixture of 35.0 parts of 1-(2,4-dichlorophenyl)-2-(1H-imidazol-1-yl)ethanone 4-methylbenzenesulfonate (1:1) and 70.0 parts of phosphor pentabromide was stirred and refluxed for 4 hours. The reaction mixture was allowed to cool and diluted with trichloromethane. This solution was added dropwise, during a 2 hours period, to a solution of 400 parts of potassium carbonate in 500 parts of water. The whole was stirred overnight at room temperature. The product was extracted with dichloromethane. The extract was washed twice with water, dried, filtered and evaporated. The residue was purified by column chromatography over silica gel using methylbenzene as eluent. The pure fractions were collected and the eluent was evaporated. The residue was converted into the nitrate salt in 4-methyl-2-pentanone and 2,2'-oxybispropane. The salt was filtered off and purified by reversed phase chromatography over LiChroprep. RP 18 using a mixture of methanol and water (35:6 by volume). The pure fractions were collected and the eluent was evaporated. From the residue, the free base was liberated and converted again into the nitrate salt in a mixture of ethyl acetate and 2,2'-oxybispropane. The salt was filtered off and crystallized from 4-methyl-2-pentanone, yielding 2.5 parts of (E)-1-[2-bromo-2-(2,4-dichlorophenyl)ethenyl]-1H-imidazole mononitrate; mp. 144.4° C. (compound 69).

Example 17

A mixture of 35.0 parts of 1-(2,4-dichlorophenyl)-2-(1H-imidazol-1-yl)ethanone 4-methylbenzenesulfonate (1:1) and 70.0 parts of phosphor pentabromide was stirred and refluxed for 4 hours. After cooling, the reaction mixture was diluted with dichloromethane. A solution of 400 parts of potassium carbonate in 500 parts of water was added dropwise during a 2 hour period while stirring. Upon completion, stirring was continued overnight. The product was extracted with dichloromethane (pH≧9–10). The organic layer was washed with water, dried, filtered and evaporated in vacuo. The residue was purified by column chromatography over silica gel using methylbenzene as eluent. The third fraction was collected and the eluent was evaporated in vacuo. The residue was converted into the nitrate salt in a mixture of 4-methyl-2-pentanone and 2,2'-oxybispropane. The salt was filtered off and purified by reversed phase chromatography (HPLC) over LiChroprep. 18 using a mixture of 70% of methanol containing 0.1% of N-(1-methylethyl)-2-propanamine and 30% of water containing 0.5% of ammonium acetate. The pure fractions were collected and the eluent was evaporated. The residue was crystallized from 2-propanol, yielding 2.5 parts of (E)-1-[2-bromo-2-(2,4-dichlorophenyl)ethenyl]-1H-imidazole mononitrate; mp. 148.3° C. (compound 70).

What is claimed is:

1. A chemical compound having the formula

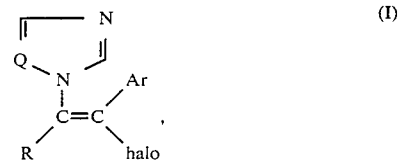

a pharmaceutically acceptable acid addition salt or a stereochemically isomeric forms thereof, wherein
Q is CH or N;
R is hydrogen, lower alkyl, aryl, aryllower alkyl or halo; and
Ar is aryl;
wherein aryl is phenyl, substituted phenyl, naphthalenyl, substituted naphthalenyl, thienyl or substituted thienyl, wherein said substituted naphthalenyl and substituted thienyl are naphthalenyl, respectively thienyl, having 1 or 2 substituents each independently selected from the group consisting of halo, lower alkyl and lower alkyloxy and wherein said substituted phenyl is phenyl having from 1 to 3 substituents each independently selected from the group consisting of halo, lower alkyl, lower alkyloxy, trifluoromethyl, nitro, amino, phenyllower alkyl and a radical $R^2$, said $R^2$ being phenyl optionally substituted with halo and/or lower alkyl; provided that not more than one substituent on said substituted phenyl is a radical $R^2$.

2. A chemical compound according to claim 1 wherein Ar is phenyl being substituted with 1 or 2 halo atoms.

3. A chemical compound according to claim 1 wherein Q is CH and Ar is phenyl substituted with 1 or 2 halo atoms.

4. A chemical compound according to claim 1 wherein the compound of formula-(I) is 1-[2-chloro-2-(2,4-dichlorophenyl)ethenyl]-1H-imidazole.

5. An anticonvulsant composition comprising an inert carrier and an anticonvulsant effective amount of a compound having the formula

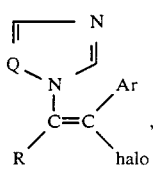

(I)

a pharmaceutically acceptable acid addition salt or a stereochemically isomeric form thereof, wherein
Q is CH or N;
R is hydrogen, lower alkyl, aryl, aryllower alkyl or halo; and
Ar is aryl;
wherein aryl is phenyl, substituted phenyl, naphthalenyl, substituted naphthalenyl, thienyl or substituted thienyl, wherein said substituted naphthalenyl and substituted thienyl are naphthalenyl, respectively thienyl, having 1 or 2 substituents each independently selected from the group consisting of halo, lower alkyl and lower alkyloxy and wherein said substituted phenyl is phenyl having from 1 to 3 substituents each independently selected from the group consisting of halo, lower alkyl, lower alkyloxy, trifluoromethyl, nitro, amino, phenyllower alkyl and a radical $R^2$, said $R^2$ being phenyl optionally substituted with halo and/or lower alkyl; provided that not more than one substituent on said substituted phenyl is a radical $R^2$.

6. A pharmaceutical composition according to claim 5 wherein Ar is phenyl being substituted with 1 or 2 halo atoms.

7. A pharmaceutical composition according to claim 5 wherein Q is CH and Ar is phenyl substituted with 1 or 2 halo atoms.

8. A pharmaceutical composition according to claim 5 wherein the compound of formula (I) is 1-[2-chloro-2-(2,4-dichlorophenyl)ethenyl]-1H-imidazole.

9. A method of treating warm-blooded animals suffering from convulsions which method comprises the systemic administration to said warm-blooded animals of an effective anticonvulsant amount of at least one compound having the formula

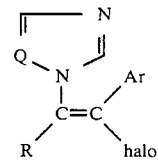

(I)

a pharmaceutically acceptable acid addition salt or a stereochemically isomeric form thereof, wherein
Q is CH or N;
R is hydrogen, lower alkyl, aryl, aryllower alkyl or halo; and
Ar is aryl;
wherein aryl is phenyl, substituted phenyl, naphthalenyl, substituted naphthalenyl, thienyl or substituted thienyl, wherein said substituted naphthalenyl and substituted thienyl are naphthalenyl, respectively thienyl, having 1 or 2 substituents each independently selected from the group consisting of halo, lower alkyl and lower alkyloxy and wherein said substituted phenyl is phenyl having from 1 to 3 substituents each independently selected from the group consisting of halo, lower alkyl, lower alkyloxy, trifluoromethyl, nitro, amino, phenyllower alkyl and a radical $R^2$, said $R^2$ being phenyl optionally substituted with halo and/or lower alkyl; provided that not more than one substituent on said substituted phenyl is a radical $R^2$.

10. A method according to claim 9 wherein Ar is phenyl being substituted with 1 or 2 halo atoms.

11. A method according to claim 9 wherein Q is CH and Ar is phenyl substituted with 1 or 2 halo atoms.

12. A method according to claim 9 wherein the compound of formula (I) is 1-[2-chloro-2-(2,4-dichlorophenyl)ethenyl]-1H-imidazole.

* * * * *